United States Patent
Martin et al.

(10) Patent No.: US 9,770,030 B2
(45) Date of Patent: Sep. 26, 2017

(54) SUSPOEMULSION OF FOMESAFEN AND FLUTHIACET-METHYL

(71) Applicants: Timothy Martin, Ringoes, NJ (US); Shiv D. Sharma, Philadelphia, PA (US); Sandra Shinn, Columbus, NJ (US)

(72) Inventors: Timothy Martin, Ringoes, NJ (US); Shiv D. Sharma, Philadelphia, PA (US); Sandra Shinn, Columbus, NJ (US)

(73) Assignee: FMC Corporation, Philadelphia, PA (US)

( * ) Notice: Subject to any disclaimer, the term of this patent is extended or adjusted under 35 U.S.C. 154(b) by 50 days.

(21) Appl. No.: 13/916,073

(22) Filed: Jun. 12, 2013

(65) Prior Publication Data
US 2014/0302990 A1 Oct. 9, 2014

Related U.S. Application Data

(60) Provisional application No. 61/807,817, filed on Apr. 3, 2013.

(51) Int. Cl.
*A01N 25/04* (2006.01)
*A01N 41/06* (2006.01)
*A01N 43/90* (2006.01)

(52) U.S. Cl.
CPC ............. *A01N 43/90* (2013.01); *A01N 41/06* (2013.01)

(58) Field of Classification Search
USPC ........................................................ 504/137
See application file for complete search history.

(56) References Cited

U.S. PATENT DOCUMENTS

| 8,575,067 B2 | 11/2013 | Yoshii et al. | |
| 2002/0004457 A1* | 1/2002 | Nevill | A01N 61/00 504/138 |
| 2003/0161856 A1* | 8/2003 | Tandt et al. | 424/405 |
| 2008/0213326 A1* | 9/2008 | Amrhein et al. | 424/405 |
| 2008/0234350 A1* | 9/2008 | Ziegler et al. | 514/407 |
| 2009/0054236 A1* | 2/2009 | Ziemer et al. | 504/103 |
| 2012/0322661 A1* | 12/2012 | Shroff et al. | 504/333 |
| 2014/0121108 A1* | 5/2014 | Yamada et al. | 504/136 |

FOREIGN PATENT DOCUMENTS

EP 1128729 B1 5/2003

OTHER PUBLICATIONS

Atlox 4913, Product Summary Sheet, Croda International 2012, 1 page [online] www.crodacropcare.com.
Atlas G-5000, Product Summary Sheet, Croda International 2013, 1 page [online] www.crodacropcare.com.
Cadet Herbicide, Product Technical Sheet, FMC Corporation, 2009, 3 pages, [online] www.fmccrop.com/grower/Products/Herbicides/Cadet.aspx.
Dow Corning AF Emulsion, Product Sheet, Dow Corning Corporation, 1998, 2 pages, [online] www.dowcorning.com.
Aromatic 200, Product Safety Summary, ExxonMobil Chemical, Apr. 2013, 3 pages [online] www.
Rhodopol 23, Product Data Sheet, Rhodia, 2 pages, Sep. 2012, [online] www.rhodia.com.
Kelzan ASX, Product Summary, CPKelco, 4 pages, 2011, [online] www.cpkelco.com.
Kathon ICP/CG, Product Summary, Rohm and Haas, 2007, 14 pages, www.dow.com/products.
Activator 90, Loveland Products Inc. Data Sheet and Label, 2 pages, 2009, [online] www.lovelandproducts.com.
Reflex Herbicide, Syngenta, Technical Data Sheet, 2 pages, 2010, [online] www.syngentacropprotection.com.

* cited by examiner

*Primary Examiner* — John Pak
*Assistant Examiner* — Luke Karpinski
(74) *Attorney, Agent, or Firm* — FMC Corporation

(57) ABSTRACT

The present invention provides novel synergistic herbicidal suspoemulsion compositions of fomesafen and fluthiacet-methyl that have superior chemical and physical stability and increased herbicidal action when compared to tank mixtures.

7 Claims, No Drawings

SUSPOEMULSION OF FOMESAFEN AND FLUTHIACET-METHYL

FIELD OF THE INVENTION

The present invention relates to the field of agrochemical suspoemulsion concentrate compositions.

BACKGROUND OF THE INVENTION

To enable the efficient elimination or controlling of unwanted plants, it is desirable to use effective chemical formulations of herbicides. Compositions containing two or more herbicides are desirable in agricultural, specialty applications and related endeavors due to broadening the spectrum or range of unwanted plant species killed or controlled.

Due to the desirability of having a composition with the above-mentioned properties, it is useful to combine herbicides to obtain enhanced control of numerous weeds with a single application. One method of preparing such a composition is referred to as "tank mixing" wherein the ingredients in their commercially available form are mixed together by the user, usually in a quantity of water. Tank mixes require the user to purchase two or more commercial formulations, store them, calculate the correct amount of each active ingredient, measure those amounts into the mix and when empty, properly dispose of a number of containers. Combining active ingredients into one pre-mix formulation is beneficial but frequently more complex due to widely different physical properties of the active ingredients in which chemical and physical stability are problems.

Fomesafen, the common name for 5-[2-chloro-4-(trifluoromethyl)phenoxy]-N-9methylsulfonyl)-2-nitrobenzamide, is a selective post-emergence herbicide used primarily for the control of broad-leaved weeds in soybeans. Fluthiacet-methyl, the common name for methyl{2-chloro-4-fluoro-5-[(EZ)-5,6,7,8-tetrahydro-3-oxo-1H,3H-[1,3,4]thiadiazolo[3,4-α]pyridazin-1-ylideneamino]phenylthio}acetate, a highly effective post-emergence herbicide used for the control of broad-leaved weeds mainly in maize and soybeans.

When used separately for post-emergence broadleaf weed control in soybean crops, fomesafen and fluthiacet-methyl do not adequately control major broadleaf weeds found in many soybean fields such as morningglory, water hemp and lambs quarters. Tank mixing the commercially available formulations of these actives slightly improves the control of these major weed species.

It would be most beneficial to provide chemically and physically stable pre-mix formulations of fomesafen and fluthiacet-methyl that improve the herbicidal activity of the mixture allowing the use of lower rates of each active.

SUMMARY OF THE INVENTION

The present invention provides novel herbicidal suspoemulsion compositions of fomesafen and fluthiacet-methyl that have superior chemical and physical stability and increased herbicidal action when compared to tank mixtures.

DETAILED DESCRIPTION OF THE INVENTION

The present invention provides novel herbicidal suspoemulsion compositions of fomesafen and fluthiacet-methyl that have superior chemical and physical stability and increased herbicidal action when compared to tank mixtures.

In one aspect of the present invention there is provided a suspoemulsion composition comprising: a) an aqueous suspension concentrate composition of fomesafen and b) an emulsion in water composition of fluthiacet-methyl.

The suspension concentrate composition comprises:
i) solid fomesafen;
ii) a surfactant component;
iii) a dispersant component
iv) an antifreeze agent;
v) an antifoam agent;
vi) a preservative; and
vii) a thickening agent.

The emulsion in water composition comprises:
i) fluthiacet-methyl;
ii) a solvent;
iii) a surfactant component;
iv) a dispersant component
v) an antifreeze agent;
vi) an antifoam agent;
vii) a preservative;
viii) a thickening agent; and
ix) an acid.

The suspoemulsion composition is formed by combining the suspension concentrate and the emulsion in water composition and stirring the mixture until homogenous.

In the suspension concentrate portion of the present invention, it is preferred that the fomesafen is present in an amount of 35% to 40% by weight of all the components in the suspension concentrate. The surfactant component is preferably an acrylic copolymer, for example, Atlox™ 4913, available from Croda Crop Care, present in an amount of 3% to 4% by weight of all the components in the suspension concentrate. The dispersant component is preferably a polyalkylene oxide block copolymer, for example, Atlas™ G-5000, available from Croda Crop Care, present in an amount of 2% to 3% by weight of all the components in the suspension concentrate. The antifreeze agent is preferably propylene glycol, present in an amount of 5% to 7% by weight of all the components in the suspension concentrate. The antifoam agent is preferably a silicone emulsion, for example, DOWCORNING® AF Emulsion available from Dow Corning Corporation, present in an amount of about 0.1% by weight of all the components in the suspension concentrate. The preservative (or microbiocide) is preferably KATHON™ GC/ICP or LEGEND® MK both available from Rohm and Haas Corporation, present in an amount of about 0.15% by weight of all the components in the suspension concentrate. The thickening agent is preferably a xanthan gum, for example, RHODOPOL 23 brand of xanthan gum, available from Rhone-Poulenc, Inc. or KELZAN® M, available from CP Kelco A Huber Company, present in an amount of about 0.1% to 0.2% by weight of all the components in the suspension concentrate.

In the emulsifiable concentrate portion of the present invention, it is preferred that fluthiacet-methyl is present in an amount of 1% to 2% by weight of all the components in the emulsifiable concentrate. The solvent is preferably naphthalene depleted aromatic solvent, for example, ExxonMobile™ Aromatic 200 ND, present in an amount of 45% to 55% by weight of all the components in the emulsifiable concentrate. The surfactant component is preferably an acrylic copolymer, for example, Atlox™ 4914, available from Croda Crop Care, present in an amount of 4% to 5% by weight of all the components in the emulsifiable concentrate. The dispersant component is preferably a polyalkylene oxide block copolymer, for example, Atlas™ G-5000, available from Croda Crop Care, present in an amount of 4% to 6% by weight of all the components in the emulsifiable concentrate. The antifreeze agent is preferably propylene glycol, present in an amount of 5% to 7% by weight of all the components in the emulsifiable concentrate. The antifoam agent is preferably a silicone emulsion, for example, DOWCORNING® AF Emulsion available from Dow Corning Corporation, present in an amount of about 0.05% by weight of all the components in the emulsifiable concentrate. The preservative (or microbiocide) is preferably KATHON™ GC/ICP or LEGEND® MK both available from Rohm and Haas Corporation, present in an amount of about 0.15% by weight of all the components in the emulsifiable concentrate. The thickening agent is preferably a xanthan gum, for example, RHODOPOL 23 brand of xanthan gum, available from Rhone-Poulenc, Inc. or KELZAN® ASX, available from CP Kelco A Huber Company, present in an amount of 0.01% to 1.0% weight of all the components in the emulsifiable concentrate. The acid is preferably acetic acid, used to adjust the pH of the emulsifiable concentrate, and is present in an amount of 0.01% to 0.1% by weight of all the components in the emulsifiable concentrate.

In the present invention, solid fomesafen suspension concentrate is milled to a small particle size in order to prevent clogging spray nozzles. The preferred particle size is about 10 microns or less, achieved by milling an aqueous mixture containing fomesafen in, for example, an Eiger mill The ratio of fomesafen to fluthiacet-methyl salt can vary over a wide range but is usually in the range of 17:1 to 35:1, preferably 20:1 to 28:1, most preferably 24:1 to 26:1.

A particular embodiment of the present invention is a method for the control of unwanted plants comprising applying a pesticidally effective amount of the composition of the present invention to an area where such control is desired.

As used in this specification and, unless otherwise indicated, the term "herbicide" refers to a molecule or combination of molecules that inhibits or otherwise kills unwanted plants, such as, but not limited to, deleterious or annoying weeds, broadleaf plants, grasses and sedges and can be used for crop protection, edifice protection or turf protection. The term "herbicidally effective amount" means an amount necessary to produce an observable herbicidal effect on unwanted plant growth, including the effects of necrosis, death, growth inhibition, reproduction inhibition, inhibition of proliferation, and removal, destruction, or otherwise diminishing the occurrence and activity of unwanted plants.

In another aspect, the present invention provides a preferred method for selective control of broadleaf weeds such as Morningglory, Waterhemp, Lambsquarters and Velvetleaf in soybean fields, said method comprising applying an herbicidal suspoemulsion composition of the present invention comprising fomesafen and fluthiacet-methyl in a ratio of from 17:1 to 35:1, preferably 20:1 to 28:1, most preferably 24:1 to 26:1at a rate of from 60.44 g/ha to 232.5 g/ha of fomesafen in combination with from 2.66 g/ha to 8.92 g/ha of fluthiacet-methyl to a locus where weeds are present.

The terms "ambient temperature" and "room temperature" as utilized herein shall generally mean any suitable temperature found in a laboratory or other working quarter, and is generally neither below about 15° C. nor above about 30° C.

As used herein, "% by weight of components in the total composition" includes the wt % of all liquid and solid components in the composition.

The process and compositions of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

Preparation of a Suspoemulsion Concentrate
Formulation of Fomesafen and Fluthiacet-methyl Step A: Fomesafen Suspension Concentrate (SC)

Into a one liter beaker was placed 299.64 grams of deionized water, 20.30 grams of an acrylic copolymer surfactant (Altox™ 4913), 29.00 grams of propylene glycol, 0.80 gram of a silicone emulsion (DOWCORNING® AF Emulsion), 14.20 grams of a polyalkylene oxide block copolymer (Atlas™ G-5000) and 227.93 grams of fomesafen (98.8% purity). The mixture was blended in a mixer at 2400 rpm for 15 minutes. The mixture was transferred to a Silverson homogenizer and homogenized for 2.5 minutes at 8000 rpm. The homogenized mixture was transferred to an Eiger mill and milled for 25 minutes at 3600rpm. The particle size was determined, using a Horiba Laser Scattering Particle Size Distribution Analyzer, to be D(90) 2.65 microns. The mixture was filtered to remove the milling media. To the filtrate was added a solution of 0.91 gram of a preservative (KATHON™ GC/ICP) and 0.90 gram of xanthan gum (Kelzan M) in 7.00 grams of propylene glycol was added and stirred until a uniform mixture was obtained, yielding 547.14 grams of an SC composition, identified as Step A, Sample 1.

Step A was repeated using the same quantities of reagents to yield 549.51 grams of an SC composition identified as Step A, Sample 2.

Step B: Fluthiacet-methyl Emulsifiable Concentrate (EC)

Into a 15 liter jacketed reaction vessel equipped with an inline homogenizer and re-circulating pump was added 5.37715 kilograms of deionized water, 7.65 grams of acetic acid and 13.75 grams of xanthan gum (KELZAN® ASX). The mixture was stirred at ambient temperature until all the xanthan gum was dissolved. Propylene glycol (917.0 grams), 7.65 grams of a silicone emulsion (DOWCORNING® AF Emulsion), 764.15 grams of a polyalkylene oxide block copolymer (Atlas™ G-5000) and 22.9 grams of a preservative (KATHON™ GC/ICP) was added and the resultant mixture stirred at ambient temperature for about 18 hours. This mixture is designated the aqueous phase.

SE composition contained 15.2% by weight fomesafen and 0.61% by weight fluthiacet-methyl.

TABLE 1

Stability Data From Example 1

| | | Stability Time Station and Conditions | | | |
|---|---|---|---|---|---|
| | Initial | 2 Weeks at 54° C. | 1 Month at Room Temperature | 3 Months at Room Temperature | 6 Months at Room Temperature |
| | | Separation of Phases | | | |
| | zero % | Slight internal phase separation visible | Slight internal phase separation visible | Slight internal phase separation visible | Slight internal phase separation visible |
| Pour Outs Dilution Stability- number of inversions for re-suspension | zero | 2 | 3 | 2 | 2 |
| 20 ppm 1 hour | 3 | 3 | 3 | 3 | 3 |
| 20 ppm 24 hours | 5 | 4 | 4 | 6 | 5 |
| 342 ppm 1 hour | 3 | 2 | 3 | 3 | 3 |
| 342 ppm 24 hours | 4 | 3 | 4 | 5 | 5 |

An organic phase was prepared by adding 7.25945 kilograms of Aromatic 200 ND and 187.4 grams of fluthiacet-methyl (99.9% purity) to a mixing vessel and the mixture stirred at ambient temperature until all solids were dissolved. An acrylic copolymer (725.95 grams of Altox™ 4914) was added and the mixture was heated to 60° C. while stiffing for about 18 hours.

The aqueous phase was warmed to 60° C. and the re-circulating pump and homogenizer were turned on and the warm organic phase was added to the re-circulation line through a feed pump. Upon complete addition the mixture was homogenized until a particle size of less than 3 microns (D (90)) was achieved. The homogenizer was turned off and the mixture allowed to cool to cool to ambient temperature using slow agitation.

Step B was repeated using the same amounts of reagents to form a second batch of Fluthiacet-methyl EC. The batches were combined and stored in a 10 gallon steel drum, final particle size, D (90) was 2.02 microns.

Step C: Fomesafen and Fluthiacet-methyl Suspoemulsion (SE)

1) 17:1 Ratio

Into a 1 liter beaker was added 182.0 grams of fomesafen SC from Step A, Sample 1, 286.6 grams of fluthiacet-methyl EC from Step B and 31.3 grams of an aqueous 2% xanthan gum solution. The mixture was stirred until a homogenous mixture was obtained. Analysis by HPLC indicated that the SE composition contained 12.7% by weight fomesafen and 0.74% by weight fluthiacet-methyl.

2) 25:1 Ratio

Into a 1 liter beaker was added 223.8 grams of fomesafen SC from Step A, Sample 1, 244.5 grams of fluthiacet-methyl EC from Step B and 31.3 grams of an aqueous 2% xanthan gum solution. The mixture was stirred until a homogenous mixture was obtained. Analysis by HPLC indicated that the

EXAMPLE 2

Post-Emergent Herbicidal Evaluation of Fomesafen and Fluthiacet-Methyl SE Compositions Compositions of the present invention were tested for herbicidal efficacy in the following manner:

Test compositions containing fomesafen and fluthiacet-methyl SE compositions of the present invention as well as commercial formulations of fomesafen (Reflex™ Herbicide available from Syngenta Crop Protection, Inc), fluthiacet-methyl (Cadet™ Herbicide available from FMC Corporation) and tank mixtures of the commercial formulations, were diluted with water to provide the appropriate test rate concentrations.

Seeds of Morningglory (*Ipomoea hederacea*), Waterhemp (*Amaranthus rudis*), Lambsquarters (*Chenopodium album*) and Velvetleaf (*Abutilon theophrasti*) were planted in 3 inch plastic pots containing Metromix 360 potting mix (available from SunGro horticultural Products). Test weeds were about 8-10 cm tall and soybean plants were at the 2-3 trifoliate leaf stage at the time of treatment. All spray solutions were applied in water with 0.25% v/v non-ionic surfactant (Activator 90™ available from Loveland Products, Inc) using a Devries™ track sprayer set for 281 L/ha. Control of weeds was evaluated at 4, 7 and 14 days after treatment (DAT) for each test rate. Four replications were made for each test rate along with an untreated control. In order to provide a measure of the effectiveness of a herbicide's performance weed control ratings were based on visual observations on a 0 to 100 rating system, where 0 equals no control and 100 equals complete control. In this system the standard basis for comparison is the untreated control.

The averaged results are in Table 2 below.

TABLE 2

Percent Control of Weeds With Post-emergent Applications of Sulfentrazone, Metsulfuron Methyl and Mixtures Thereof

| | Rate of application | | **Expected calculation | % Control of Weeds | | |
|---|---|---|---|---|---|---|
| | | | | Days After Treatment - Morningglory Control | | |
| *Treatment | lb/ac | Ratio | see footnote | 3 | 7 | 14 |
| Untreated Control | N/A | | | 0 | 0 | 0 |
| Fomesafen (Reflex Herbicide) | 93.0 | | | 69 | 72 | 55 |
| | 133.6 | | | 72 | 72 | 69 |
| | 175.1 | | | 70 | 74 | 55 |
| | 222.3 | | | 81 | 75 | 78 |
| Fluthiacet methyl (Cadet Herbicide) | 1.6 | | | 86 | 70 | 73 |
| | 3.1 | | | 85 | 80 | 71 |
| | 5.1 | | | 89 | 85 | 75 |
| | 6.3 | | | 89 | 87 | 76 |
| Reflex Herbicide + Cadet Herbicide Tank Mix | 95.8 (93.2/2.6) | 35:1 | Observed | 84 | 78 | 72 |
| | 143.6 (139.6/4.0) | 35:1 | Observed | 81 | 80 | 78 |
| | 191.5 (186.2/5.3) | 35:1 | Observed | 87 | 81 | 85 |
| | 239.1 (232.5/6.6) | 35:1 | Observed | 89 | 89 | 79 |
| Example 1C-1 | 95.8 (93.2/2.6) | 35:1 | Observed | 99 | 99 | 100 |
| | 143.6 (139.6/4.0) | 35:1 | Observed | 99 | 99 | 100 |
| | 191.5 (186.2/5.3) | 35:1 | Observed | 99 | 99 | 100 |
| | 239.1 (232.5/6.6) | 35:1 | Observed (Expected) | 99 (98) | 99 (97) | 100 (95) |
| Example 1C-2 | 75.8 (72.9/2.9) | 25:1 | Observed | 99 | 99 | 100 |
| | 113.7 (109.3/4.4) | 25:1 | Observed | 99 | 99 | 100 |
| | 151.6 (145.8/5.8) | 25:1 | Observed | 99 | 99 | 100 |
| | 180.5 (182.2/7.3) | 25:1 | Observed | 99 | 99 | 100 |
| Example 1C-3 | 65.0 (60.4/3.6) | 17:1 | Observed | 99 | 99 | 100 |
| | 96.3 (91.0/5.3) | 17:1 | Observed | 99 | 99 | 100 |
| | 128.4 (121.3/7.1) | 17:1 | Observed | 99 | 99 | 100 |
| | 160.5 (151.6/8.9) | 17:1 | Observed | 99 | 99 | 100 |

| | Rate of application | | **Expected calculation | % Control of Weeds | | |
|---|---|---|---|---|---|---|
| | | | | Days After Treatment - Water Hemp Control | | |
| *Treatment | lb/ac | Ratio | see footnote | 3 | 7 | 14 |
| Untreated Control | N/A | | | 0 | 0 | 0 |
| Fomesafen (Reflex Herbicide) | 93.0 | | | 43 | 65 | 43 |
| | 133.6 | | | 35 | 62 | 45 |
| | 175.1 | | | 38 | 65 | 52 |
| | 222.3 | | | 39 | 65 | 50 |
| Fluthiacet methyl (Cadet Herbicide) | 1.6 | | | 38 | 68 | 44 |
| | 3.1 | | | 38 | 65 | 48 |
| | 5.1 | | | 38 | 68 | 46 |
| | 6.3 | | | 40 | 62 | 45 |
| Reflex Herbicide + Cadet Herbicide Tank Mix | 95.8 (93.2/2.6) | 35:1 | Observed | 35 | 61 | 42 |
| | 143.6 (139.6/4.0) | 35:1 | Observed | 36 | 65 | 45 |
| | 191.5 (186.2/5.3) | 35:1 | Observed | 37 | 67 | 46 |
| | 239.1 (232.5/6.6) | 35:1 | Observed | 40 | 68 | 66 |

TABLE 2-continued

Percent Control of Weeds With Post-emergent Applications
of Sulfentrazone, Metsulfuron Methyl and Mixtures Thereof

| Treatment | Rate (lb/ac) | Ratio | Expected calculation | | | |
|---|---|---|---|---|---|---|
| Example 1C-1 | 95.8 (93.2/2.6) | 35:1 | Observed | 70 | 85 | 92 |
| | 143.6 (139.6/4.0) | 35:1 | Observed | 67 | 75 | 78 |
| | 191.5 (186.2/5.3) | 35:1 | Observed | 54 | 71 | 78 |
| | 239.1 (232.5/6.6) | 35:1 | Observed (Expected) | 61 (63) | 86 (87) | 88 (73) |
| Example 1C-2 | 75.8 (72.9/2.9) | 25:1 | Observed | 54 | 72 | 77 |
| | 113.7 (109.3/4.4) | 25:1 | Observed | 67 | 79 | 82 |
| | 151.6 (145.8/5.8) | 25:1 | Observed | 75 | 85 | 86 |
| | 180.5 (182.2/7.3) | 25:1 | Observed | 75 | 82 | 86 |
| Example 1C-3 | 65.0 (60.4/3.6) | 17:1 | Observed | 76 | 76 | 80 |
| | 96.3 (91.0/5.3) | 17:1 | Observed | 86 | 79 | 87 |
| | 128.4 (121.3/7.1) | 17:1 | Observed | 77 | 88 | 87 |
| | 160.5 (151.6/8.9) | 17:1 | Observed | 80 | 87 | 88 |

| *Treatment | Rate of application lb/ac | Ratio | **Expected calculation see footnote | % Control of Weeds Days After Treatment - Lambs Quarter Control | | |
|---|---|---|---|---|---|---|
| | | | | 3 | 7 | 14 |
| Untreated Control | N/A | | | 0 | 0 | 0 |
| Fomesafen (Reflex Herbicide) | 93.0 | | | 41 | 65 | 45 |
| | 133.6 | | | 43 | 71 | 54 |
| | 175.1 | | | 41 | 72 | 55 |
| | 222.3 | | | 41 | 74 | 63 |
| Fluthiacet methyl (Cadet Herbicide) | 1.6 | | | 43 | 69 | 69 |
| | 3.1 | | | 45 | 75 | 78 |
| | 5.1 | | | 41 | 74 | 77 |
| | 6.3 | | | 32 | 72 | 73 |
| Reflex Herbicide + Cadet Herbicide Tank Mix | 95.8 (93.2/2.6) | 35:1 | Observed | 41 | 68 | 69 |
| | 143.6 (139.6/4.0) | 35:1 | Observed | 41 | 73 | 67 |
| | 191.5 (186.2/5.3) | 35:1 | Observed | 43 | 72 | 76 |
| | 239.1 (232.5/6.6) | 35:1 | Observed | 43 | 72 | 72 |
| Example 1C-1 | 95.8 (93.2/2.6) | 35:1 | Observed | 77 | 74 | 81 |
| | 143.6 (139.6/4.0) | 35:1 | Observed | 75 | 74 | 80 |
| | 191.5 (186.2/5.3) | 35:1 | Observed | 68 | 75 | 81 |
| | 239.1 (232.5/6.6) | 35:1 | Observed (Expected) | 69 (60) | 80 (93) | 84 (90) |
| Example 1C-2 | 75.8 (72.9/2.9) | 25:1 | Observed | 68 | 77 | 77 |
| | 113.7 (109.3/4.4) | 25:1 | Observed | 70 | 76 | 80 |
| | 151.6 (145.8/5.8) | 25:1 | Observed | 74 | 78 | 84 |
| | 180.5 (182.2/7.3) | 25:1 | Observed | 73 | 78 | 78 |
| Example 1C-3 | 65.0 (60.4/3.6) | 17:1 | Observed | 76 | 76 | 81 |
| | 96.3 (91.0/5.3) | 17:1 | Observed | 73 | 80 | 86 |
| | 128.4 (121.3/7.1) | 17:1 | Observed | 74 | 82 | 82 |
| | 160.5 (151.6/8.9) | 17:1 | Observed | 78 | 81 | 85 |

TABLE 2-continued

Percent Control of Weeds With Post-emergent Applications
of Sulfentrazone, Metsulfuron Methyl and Mixtures Thereof

|  |  |  |  | % Control of Weeds | | |
|---|---|---|---|---|---|---|
|  | Rate of application |  | **Expected calculation | Days After Treatment - Velvet Leaf Control | | |
| *Treatment | lb/ac | Ratio | see footnote | 3 | 7 | 14 |
| Untreated Control | N/A |  |  | 0 | 0 | 0 |
| Fomesafen (Reflex Herbicide) | 93.0 |  |  | 76 | 75 | 41 |
|  | 133.6 |  |  | 83 | 68 | 45 |
|  | 175.1 |  |  | 85 | 87 | 75 |
|  | 222.3 |  |  | 86 | 70 | 57 |
| Fluthiacet methyl (Cadet Herbicide) | 1.6 |  |  | 88 | 88 | 78 |
|  | 3.1 |  |  | 87 | 93 | 92 |
|  | 5.1 |  |  | 97 | 97 | 99 |
|  | 6.3 |  |  | 95 | 99 | 99 |
| Reflex Herbicide + Cadet Herbicide Tank Mix | 95.8 (93.2/2.6) | 35:1 |  | 87 | 87 | 83 |
|  | 143.6 (139.6/4.0) | 35:1 |  | 89 | 98 | 99 |
|  | 191.5 (186.2/5.3) | 35:1 |  | 95 | 99 | 96 |
|  | 239.1 (232.5/6.6) | 35:1 |  | 96 | 99 | 88 |
| Example 1C-1 | 95.8 (93.2/2.6) | 35:1 | Observed | 97 | 99 | 100 |
|  | 143.6 (139.6/4.0) | 35:1 | Observed | 92 | 99 | 100 |
|  | 191.5 (186.2/5.3) | 35:1 | Observed | 96 | 99 | 99 |
|  | 239.1 (232.5/6.6) | 35:1 | Observed (Expected) | 94 (99) | 99 (100) | 100 (100) |
| Example 1C-2 | 75.8 (72.9/2.9) | 25:1 | Observed | 99 | 99 | 100 |
|  | 113.7 (109.3/4.4) | 25:1 | Observed | 95 | 98 | 100 |
|  | 151.6 (145.8/5.8) | 25:1 | Observed | 93 | 99 | 100 |
|  | 180.5 (182.2/7.3) | 25:1 | Observed | 99 | 99 | 100 |
| Example 1C-3 | 65.0 (60.4/3.6) | 17:1 | Observed | 98 | 99 | 100 |
|  | 96.3 (91.0/5.3) | 17:1 | Observed | 99 | 99 | 100 |
|  | 128.4 (121.3/7.1) | 17:1 | Observed | 98 | 99 | 100 |
|  | 160.5 (151.6/8.9) | 17:1 | Observed | 98 | 99 | 100 |

Highlighted numbers indicate synergistic herbicidal properties.
*A non-ionic surfactant (NIS) was added to each test solution, 0.25% V/V.
**Expected calculated from 222.3 lb/ac fomesafen and 6.3 lb/ac fluthiacet-methyl observed As can be seen from the data above, the suspoemulsion of the present invention exhibits greatly enhanced herbicidal activity on weeds commonly found in soybean crops such as morningglory, water hemp, Lambsquarters and velvetleaf when compared to tank mixes of commercially available formulations of fomesafen and fluthiacet-methyl.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A suspoemulsion composition comprising: a) an aqueous suspension concentrate composition of solid fomesafen as the sole active herbicidal ingredient and b) an emulsion composition of fluthiacet-methyl as the sole active herbicidal ingredient wherein the weight ratio of fomesafen to fluthiacet-methyl is from 35:1 to 17:1.

2. The composition of claim 1 wherein:
(a) the suspension concentrate composition further comprises:
  i) a surfactant component;
  ii) a dispersant component
  iii) an antifreeze agent;
  iv) an antifoam agent;
  v) a preservative;
  vi) a thickening agent; and
(b) the emulsion composition further comprises:
  i) a solvent;
  ii) a surfactant component;
  iii) a dispersant component
  iv) an antifreeze agent;
  v) an antifoam agent;

vi) a preservative;
vii) a thickening agent; and
viii) an acid.

3. The composition of claim 1 in which the ratio of fomesafen to fluthiacet-methyl is from 24:1 to 26:1.

4. The composition of claim 1 wherein fomesafen is present in an amount of 35% to 40% by weight of all the components in the suspension concentrate.

5. The composition of claim 1 wherein fluthiacet-methyl is present in an amount of 1% to 2% by weight of all the components in the emulsion.

6. The composition of claim 1 wherein the suspension concentrate comprises a surfactant component present in an amount of 3% to 4% by weight of all the components in the suspension concentrate, a dispersant component present in an amount of 2% to 3% by weight of all the components in the suspension concentrate, an antifreeze agent present in an amount of 5% to 7% by weight of all the components in the suspension concentrate, an antifoam agent present in an amount of about 0.1% by weight of all the components in the suspension concentrate, a preservative present in an amount of about 0.15% by weight of all the components in the suspension concentrate and a thickening agent present in an amount of about 0.1% to 0.2% by weight of all the components in the suspension concentrate.

7. The composition of claim 1 wherein the emulsion comprises a solvent present in an amount of 45% to 55% by weight of all the components in the emulsion, a surfactant component present in an amount of 4% to 5% by weight of all the components in the emulsion, a dispersant component present in an amount of 4% to 6% by weight of all the components in the emulsion, an antifreeze agent present in an amount of 5% to 7% by weight of all the components in the emulsion, an antifoam agent present in an amount of about 0.05% by weight of all the components in the emulsion, a preservative present in an amount of about 0.15% by weight of all the components in the emulsion, a thickening agent present in an amount of 0.01% to 1.0% weight of all the components in the emulsion and an acid present in an amount of 0.01% to 0.1% by weight of all the components in the emulsion.

* * * * *